United States Patent
Meudt et al.

(10) Patent No.: US 6,392,051 B2
(45) Date of Patent: May 21, 2002

(54) PROCESS FOR PREPARING 4-(4'-CARBOXYPHENYL)PYRIDINE

(75) Inventors: Andreas Meudt, Flörsheim-Weilbach; Stefan Scherer, Büttelborn; Peter Koch, Frankfurt am Main; Gerhard Demmer, Kelkheim; Frank Vollmüller, Frankfurt am Main, all of (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/784,535

(22) Filed: Feb. 15, 2001

(30) Foreign Application Priority Data

Feb. 15, 2000 (DE) .......................................... 100 06 601

(51) Int. Cl.$^7$ ............................................ C07D 211/70
(52) U.S. Cl. ....................................................... 546/342
(58) Field of Search .......................................... 546/342

(56) References Cited

FOREIGN PATENT DOCUMENTS

| WO | WO97/24118 | 7/1997 |
| WO | 9724118 | * 10/1997 |

OTHER PUBLICATIONS

EPO Search Report Application No. EP 01102381, Mailed May 17, 2001.

D.L. Comins, et al., ""Regioselective addition of Grignard Reagents to 1–Acylpyridinium salts. A Convenient Method for the Synthesis of 4–Alkyl (aryl) pyridines"—XP–00996215", Journal of Organic Chemistry, vol. 47 (No. 22), p. 4315–4319, (Oct. 22, 1982).

Kin–Ya Akiba, et al., ""Regioselective Synthesis of 4–Alkylpyridines Via, 1, 4–Dihydropyridine Derivatives From Pyridine"—XP–00996539", Tetrahedron Letters, Pergamon Press (Ukraine), vol. 23 (No. 4), p. 429–432, (1982).

* cited by examiner

*Primary Examiner*—Alan L. Rotman
*Assistant Examiner*—Binta Robinson
(74) *Attorney, Agent, or Firm*—Scott E. Hanf

(57) ABSTRACT

The invention relates to a process for preparing 4-(4'-carboxyphenyl)pyridine, which comprises oxidizing a 4-phenyl-N-acyldihydropyridine of the formula (II)

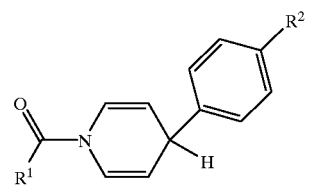

(II)

where $R^1$ is a bulky alkyl, alkylaryl, arylalkyl or alkoxy group and $R^2$ is a straight-chain or branched, substituted or unsubstituted alkyl radical having from 1 to 8 carbon atoms, by means of an oxidizing agent selected from the group consisting of permanganates, nitric acid, Cr(VI) compounds, oxygen and air to give the compound of the formula (I)

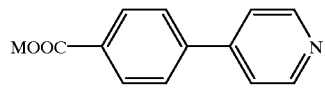

(I)

where M is a cation.

12 Claims, No Drawings

PROCESS FOR PREPARING 4-(4'-CARBOXYPHENYL)PYRIDINE

FIELD OF THE INVENTION

The invention relates to a novel process for preparing 4-(4'-carboxyphenyl)-pyridine of the formula (I).

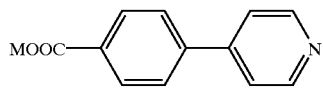

(I)

BACKGROUND OF THE INVENTION 4-(4'-Carboxyphenyl)pyridine of the formula (I) and the corresponding esters and acid chlorides are important intermediates in the synthesis of active compounds for the pharmaceutical and agrochemical industries.

Possible synthetic routes to compounds of the formula (I) are the Suzuki coupling of 4-halopyridines with suitable organometallic reagents, for example 4-carboxyphenylboronic acid or 4-carboxyphenylboronic esters. However, such pyridines, for example, 4-bromopyridine or 4-chloropyridine, are firstly very expensive and difficult-to-obtain raw materials which are also unstable in pure form and can be used only in the form of derivatives, for example as hydrochloride. Secondly, they are very corrosive and place high demands on the materials of construction used.

It is an object of the present invention to develop a process for preparing 4-(4'-carboxyphenyl)pyridine of the formula (I) which makes it possible to obtain the target compound in very few, technically simple steps starting from readily available and inexpensive raw materials. Furthermore, the process to be developed has to give the target product in a good total yield and in a purity sufficient for pharmaceutical applications.

DESCRIPTION OF THE PREFERRED EMBODIMENTS

It has surprisingly been found that the compound of the formula (I) can be prepared in good total yields and in good purity in few steps starting from pyridine. The individual steps can each be carried out in a technically simple manner and use only commercially available and inexpensive reagents, solvents and catalysts.

The present invention provides a process for preparing 4-(4'-carboxyphenyl)pyridine, which comprises oxidizing a 4-phenyl-N-acyldihydropyridine of the formula (II)

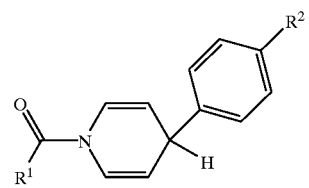

(II)

where $R^1$ is a bulky alkyl, alkylaryl, arylalkyl or alkoxy group and $R^2$ is a straight-chain or branched, substituted or unsubstituted alkyl radical having from 1 to 8 carbon atoms, by means of an oxidizing agent selected from the group consisting of permanganates, nitric acid, Cr(VI) compounds, oxygen and air to give the compound of the formula (I)

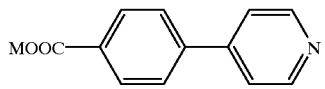

(I)

where M is a cation, preferably hydrogen, ammonium or an alkali metal cation.

Preferred radicals $R^1$ are tert-butyl, isopropyl, (dimethyl)phenylmethyl, methyl(diphenyl)methyl, trityl, diphenylmethyl, triethylmethyl, tert-butoxy and isopropoxy.

Preferred radicals $R^2$ are straight-chain or branched alkyl radicals which have from 1 to 4 carbon atoms and may be unsubstituted or substituted by one or more hydroxy or $C_1$-$C_4$-alkoxy radicals; particular preference is given to methyl, ethyl, n-propyl, i-propyl, n-butyl, methoxymethyl and hydroxymethyl, most preferably methyl.

The preparation of dihydropyridines of the formula (II) from pyridine by addition of organometallic compounds, for example Grignard compounds, cannot be carried out directly; prior activation of the pyridine ring is necessary. This can be achieved, for example, by N-acylation (Scheme 1). The N-acylpyridinium salts which can be obtained in this way do react with Grignard compounds, but the reaction gives mixtures of 2- and 4-aryldihydropyridines which are difficult to separate. According to Akiba et al., Tetrahedron Lett. 23, 4, 429-432, 1982, a high selectivity to the 4-aryldihydropyridines can be achieved by using bulky radicals on the pyridine nitrogen and using equimolar amounts of organocopper compounds. However, for a number of reasons, the preparation and handling of organocopper compounds is problematical for industrial processes.

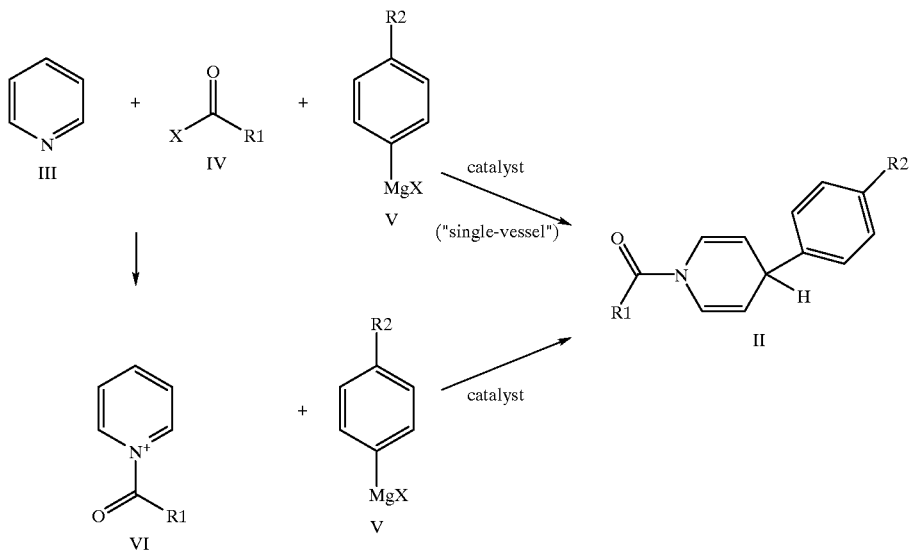

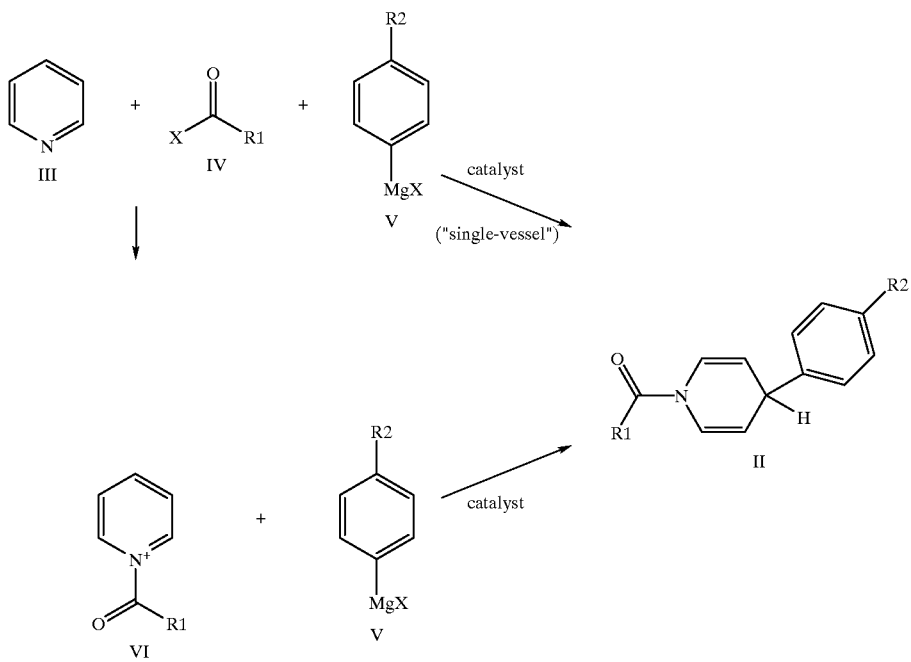

X can be Cl or Br.

The problem is solved more elegantly by Comins et al., J. Org. Chem. 1982, 47, 4315-4319. The authors react Grignard compounds with pyridine and pivaloyl chloride in the presence of catalytic amounts of CuI and obtain yields of somewhat above 60% in this way. The amounts of Cu required do not stand in the way of industrial utilization. However, such a low yield combined with the disposal problems associated with the sometimes problematical by-products resulting from the starting materials not converted into product makes the viability of the overall process questionable.

It has surprisingly been found that the addition of palladium or nickel salts or complexes or of metallic Pd or Ni as cocatalysts leads to a significant increase in yield in the preparation of a dihydropyridine of the formula (II). Yields of usually above 90%, based on the organometallic reagent used, are then achieved.

In a preferred embodiment of the process of the invention, the compound of the formula (II) is therefore prepared by acylating pyridine by means of a compound of the formula (IV) to give a compound of the formula (VI), or using a compound of the formula (VI), and coupling the compound of the formula (VI) with a Grignard compound of the formula (V) in the presence of from 0.01 to 10 mol %, preferably from 0.1 to 5 mol %, based on the Grignard compound, of a Cu compound, and in the presence of a Pd or Ni cocatalyst,

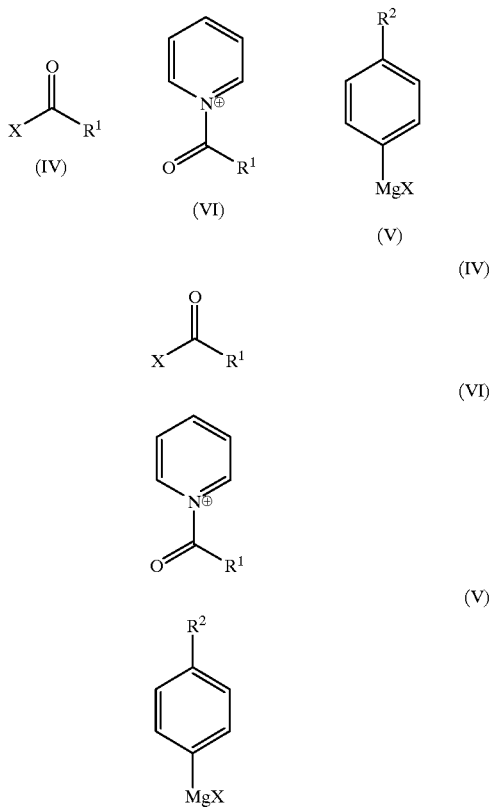

where X is Cl or Br.

Suitable solvents for the coupling of the compound of the formula (IV) with (V) are, for example, aliphatic or aromatic ethers or hydrocarbons, preferably THF or THF/toluene mixtures. The coupling can be carried out at temperatures in the range from −80° C. to the boiling point of the solvent used. However, the proportion of the 2-substitution product increases at the expense of the desired 4-substitution product at high temperatures, so that temperatures of from −70 to +60° C. are preferred. Particular preference is given to temperatures of from −50 to +50° C., particularly preferably from −35 to +40° C. Suitable Cu compounds are Cu(I) and Cu(II) compounds, preferably CuI, CuBr, CuCl or CuCl$_2$.

Suitable cocatalysts for the coupling reactions are salts, complexes or the metallic form of nickel or palladium. The amounts employed can be from $10^{-5}$ to 10 mol %, preferably from $10^{-4}$ to 7.5 mol %, in particular from 10-3 to 5 mol %, based on the Grignard compound.

Particular preference is given to salts or complexes of nickel or palladium and also metallic forms, if desired on a suitable support, e.g. Pd on C or on BaSO$_4$, very particularly preferably PdCl$_2$(dppf), PdCl$_2$(PPh$_3$)$_2$, PdCl$_2$(dppe), PdCl$_2$(dppp), PdCl$_2$(dppb), Pd(PPh$_3$)$_4$, Pd(OAc)$_2$, PdCl$_2$, PdBr$_2$ or NiCl$_2$(PPh$_3$)$_2$, where "dppf" is 1,2-bis(diphenylphosphino)ferrocene, "dppe" is 1,2-bis(diphenylphosphino)ethane, "dppp" is 1,2-bis(diphenylphosphino)propane, "dppb" is 1,2-bis(diphenylphosphino)butane, "Ph" is phenyl and "Ac" is acetyl.

The conversion of the dihydropyridine of the formula (II) into 4-(4'-carboxyphenyl)-pyridine of the formula (I) is achieved according to the invention by oxidation using an oxidizing agent selected from the group consisting of permanganates, e.g. sodium or potassium permanganate, nitric acid, chromium(VI) reagents, e.g. alkali metal chromates or alkali metal dichromates, oxygen and air, particularly preferably by air oxidation.

According to Comins et al., it is possible to convert N-acylated 4-aryldihydropyridines into the corresponding 4-arylpyridines by heating with elemental sulfur.

However, large amounts of hydrogen sulfide and other sulfur compounds are formed in the treatment with sulfur and, furthermore, high temperatures are required, resulting in a very impure, black product. This is very cumbersome to purify to the extent required for further oxidation.

It has surprisingly been found that the dihydropyridine of the formula (II) can be oxidized in a single step to give a very pure product of the formula (I). Despite the successive oxidations of the N-acyl group, of the dihydropyridine to give the pyridine and of the aromatic alkyl group to give the acid group, good yields of a pure product are obtained.

The oxidation can be carried out by means of permanganates, nitric acid, air, O$_2$, or chromium(VI) reagents; however, oxidation by means of air has been found to be particularly advantageous. Almost quantitative yields and a high purity are obtained in this way. Small amounts of the only detectable impurity, namely terephthalic acid, can be easily and quantitatively removed by washing with dilute alkalis.

The oxidation by means of permanganate can be carried out either in aqueous solution or in a nonaqueous medium, preferably at temperatures of from 0 to 100° C., in particular from 10 to 80° C. In aqueous solution, the presence of suitable phase transfer catalysts, for example tetraalkylammonium salts, tetraphenylphosphonium salts or crown ethers, is necessary to achieve good yields. The work-up is carried out by filtering off the manganese dioxide formed, acidifying the filtrate and filtering off the pyridylbenzoic acid which precipitates.

The oxidation using air or oxygen is carried out in aliphatic carboxylic acids, if desired in admixture with water. Preference is given to using acetic acid, particularly preferably a mixture of acetic acid and water. Heavy metal salts, e.g. mixtures of cobalt bromide and manganese bromide, are employed as catalysts. The heavy metal salts are used in amounts of from 0.01 to 5.0 mol % each, preferably from 0.1 to 4.0 mol % each, particularly preferably from 1.0 to 2.0 mol % each, based on the dihydropyridine (II). The ratio of cobalt to manganese can be varied within wide limits and can be, for example, from 1:5 to 5:1. The two salts are preferably used in equimolar amounts. The reaction is carried out at temperatures of from 100 to 200° C., preferably from 120 to 180° C. and particularly preferably from 150 to 170° C. The pressure is in the range from atmospheric pressure to 50 bar. The work-up is carried out by cooling and, if appropriate, concentrating the reaction mixture by evaporation, then filtering off, washing and drying the resulting precipitated carboxylic acid.

EXAMPLES

Preparation of 4-p-tolyl-N-pivaloyldihydropyridine

Example 1

1.0 mol of p-tolylmagnesium chloride (25% strength by weight solution in THF) are added dropwise at −15° C. to a solution of 121 ml of pyridine (1.5 mol), 3.8 g of CuI (0.02 mol) and 9 mg of PdCl$_2$(dppf) in 200 ml of tetrahydrofuran. Subsequently, at the same temperature, 123 ml of pivaloyl chloride (1.0 mol) are added dropwise over a period of 15 minutes. The reaction is strongly exothermic, so that good cooling is necessary. After stirring for another 15 minutes at −15° C., the cold bath is removed and the reaction mixture is stirred overnight at room temperature. After hydrolysis with 500 ml of 20% strength by weight aqueous ammonium chloride solution, extraction of the aqueous phase with toluene, drying over magnesium sulfate and distilling off the major part of the solvent, the dihydropyridine crystallizes as a colorless solid and can be obtained in very pure form by filtration. The yield of dihydropyridine is 364.7 g (1.43 mol, 95%).

Example 2

1.0 mol of p-tolylmagnesium chloride (25% strength by weight solution in THF) are added dropwise at −15° C. to a solution of 121 ml of pyridine (1.5 mol), 1.5 g of CuI (0.0079 mol) and 0.9 mg of PdCl$_2$(dppf) in 200 ml of tetrahydrofuran. Subsequently, at the same temperature, 123 ml of pivaloyl chloride (1.0 mol) are added dropwise over a period of 15 minutes. The work-up described in Example 1 gives 85% of the dihydropyridine.

Example 3

(Comparative example from D. L. Comins et al., J. Org. Chem. 1982, 47, 4315-4319)

952 mg of CuI are added at room temperature to a solution of 12.1 ml of pyridine in 200 ml of tetrahydrofuran and the mixture is stirred until a homogeneous solution has been formed. After cooling to −20° C., a solution of 0.1 mol of phenylmagnesium chloride in 50 ml of THF is added. 12.3 ml of pivaloyl chloride in 10 ml of THF are added dropwise over a period of 5 minutes. After stirring further for 15 minutes at −15° C. and another 15 minutes at room temperature, the mixture is hydrolyzed with 75 ml of 20% strength by weight ammonium chloride solution, admixed with 200 ml of ether, and the organic phase is washed in succession with 50 ml of NH$_4$Cl/NH$_4$OH 50:50, 50 ml of water, 50 ml of 10% strength HCl, 50 ml of water and 50 ml of saturated sodium chloride solution. After drying over MgSO$_4$, the solvents are distilled off in a gentle vacuum. The product remains as a yellow solid in a yield of 63%.

Example 4

Oxidation of the dihydropyridine using potassium permanganate 1.0 g of anhydrous sodium carbonate, 0.05 g of benzyltributylammonium chloride and 0.8 g of 4-p-tolyl-N-pivaloyldihydropyridine are added at room temperature to 75 ml of a 2% strength by weight aqueous potassium permanganate solution. After stirring at 100° C. for 1.5 hours, excess permanganate is reduced by means of sodium dithionite, the precipitated manganese dioxide is filtered off, the filtrate is acidified and the precipitated product is filtered off to give 4-(4'-carboxyphenyl)-pyridine in a yield of 81%.

Example 5

Oxidation of dihydropyridine using air 177.2 g (0.75 mol) of 4-p-tolyl-N-pivaloyldihydropyridine, 1511.2 g of acetic acid, 3.74 g (15.0 mmol) of cobalt(II) acetate tetrahydrate, 3.68 g (15.0 mmol) of manganese(II) acetate tetrahydrate and 3.09 g (30.0 mmol) of sodium bromide are placed in a 3.5 l autoclave. The autoclave is made inert using nitrogen and is heated to 160-165° C. When this temperature has been reached, about 450 l/h of air are introduced and an internal pressure of 16-18 bar is maintained by means of a pressure maintenance device. Air is introduced for about 30-40 minutes, the autoclave is then once again made inert by injection of nitrogen and the mixture is cooled. The greenish solution (becomes orange-red on cooling) is taken from the autoclave and evaporated to a weight of 370 g on a rotary evaporator. The thick suspension is filtered on a suction filter and the crystals are washed 3 times with 50 g each time of 75% strength by weight acetic acid. The crude product obtained in this way is taken up in 75 ml of 0.4% strength by weight sodium bicarbonate solution, stirred for 30 minutes at about 50° C. and filtered off. Drying leaves 4-(4'-carboxyphenyl)pyridine in a yield of 90%. HPLC purity: >98% (a/a).

What is claimed is:

1. A process for preparing 4-(4'-carboxyphenyl)pyridine, which comprises oxidizing a 4-phenyl-N-acyldihydropyridine of the formula (II)

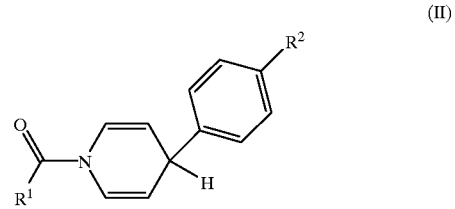

where

R$^1$ is a bulky alkyl, alkylaryl, arylalkyl or alkoxy group and

R$^2$ is a straight-chain or branched, substituted or unsubstituted alkyl radical having from 1 to 8 carbon atoms, by means of an oxidizing agent selected from the group consisting of permanganates, nitric acid, Cr(VI) compounds, oxygen and air to give the compound of the formula (I)

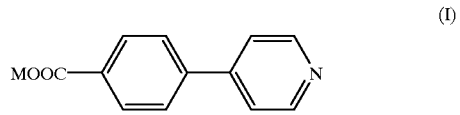

where M is a cation.

2. The process as claimed in claim 1, wherein R$^1$ is tert-butyl, isopropyl, (dimethyl)phenylmethyl, methyl (diphenyl)methyl, trityl, diphenylmethyl, triethylmethyl, tert-butoxy or isopropoxy.

3. The process as claimed in claim 1, wherein R$^2$ is methyl, ethyl, n-propyl, i-propyl, n-butyl, methoxymethyl or hydroxymethyl.

4. The process as claimed in claim 1, wherein the oxidizing agent is potassium permanganate, sodium permanganate, nitric acid, an alkali metal chromate, an alkali metal dichromate, $O_2$ or air.

5. The process as claimed in claim 1, wherein the oxidation is carried out using permanganates in the presence of phase transfer catalysts, preferably tetraalkylammonium salts, tetraphenylphosphonium salts or crown ethers.

6. The process as claimed in claim 1, wherein the oxidation is carried out using air in the presence of heavy metal salts.

7. The process as claimed in claim 6, wherein a mixture of cobalt bromide and manganese bromide is used as heavy metal salt.

8. The process as claimed in claim 1, wherein the compound of the formula (II) is prepared by acylating pyridine by means of a compound of the formula (IV) to give a compound of the formula (VI), or using a compound of the formula (VI), and coupling the compound of the formula (VI) with a Grignard compound of the formula (V) in the presence of from 0.01 to 10 mol %, preferably from 0.1 to 5 mol %, based on the Grignard compound, of a Cu compound and in the presence of a Pd or Ni cocatalyst,

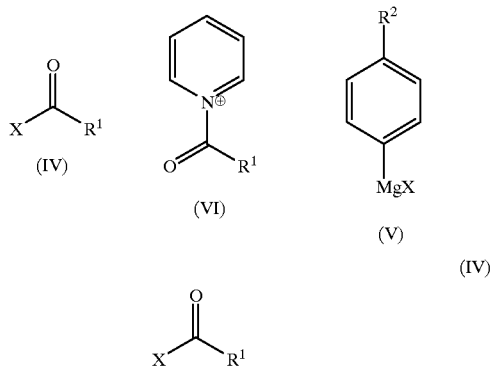

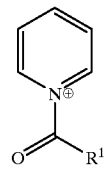

(VI)

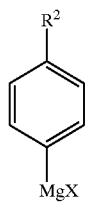

(V)

where X is Cl or Br.

9. The process as claimed in claim 8, wherein the cocatalyst is a salt, a complex or a metallic form of palladium or nickel.

10. The process as claimed in claim 8, wherein the cocatalyst is used in an amount of from 10-5 to 10 mol %, preferably from $10^{-4}$ to 7.5 mol %, based on the Grignard compound of the formula (V).

11. The process as claimed in claim 8, wherein the coupling is carried out at a temperature of from −70 to +60° C., preferably from −50 to +50° C.

12. The process as claimed in claim 8, wherein the Cu compound is CuI, CuBr, CuCl or $CuCl_2$.

* * * * *